United States Patent
Habets et al.

(10) Patent No.: US 9,014,438 B2
(45) Date of Patent: Apr. 21, 2015

(54) METHOD AND APPARATUS FEATURING SIMPLE CLICK STYLE INTERACTIONS ACCORDING TO A CLINICAL TASK WORKFLOW

(75) Inventors: Raymond J.E. Habets, Eindhoven (NL); Rutger Nijlunsing, Veldhoven (NL); Frans A. Gerritsen, Oisterwijk (NL)

(73) Assignee: Koninklijke Philips N.V., Eindhoven (NL)

( * ) Notice: Subject to any disclaimer, the term of this patent is extended or adjusted under 35 U.S.C. 154(b) by 1190 days.

(21) Appl. No.: 12/064,043

(22) PCT Filed: Aug. 16, 2006

(86) PCT No.: PCT/IB2006/052830
§ 371 (c)(1), (2), (4) Date: Feb. 18, 2008

(87) PCT Pub. No.: WO2007/020598
PCT Pub. Date: Feb. 22, 2007

(65) Prior Publication Data
US 2008/0232661 A1    Sep. 25, 2008

Related U.S. Application Data

(60) Provisional application No. 60/708,955, filed on Aug. 17, 2005.

(51) Int. Cl.
*G06T 7/00* (2006.01)
*A61B 6/00* (2006.01)
(Continued)

(52) U.S. Cl.
CPC ............... *G06T 7/0012* (2013.01); *A61B 5/055* (2013.01); *A61B 6/032* (2013.01); *A61B 6/463* (2013.01); *A61B 6/467* (2013.01); *A61B 6/469* (2013.01)

(58) Field of Classification Search
USPC .......... 382/128–132; 715/764, 766, 771, 829, 715/810, 835, 838
See application file for complete search history.

(56) References Cited

U.S. PATENT DOCUMENTS 7,050,611 B2 *  5/2006  Bodicker et al. .............. 382/128
7,640,050 B2   12/2009  Glenn, Jr. et al.
(Continued)

FOREIGN PATENT DOCUMENTS

CN     1145213 A    3/1997
CN     1282108 A    1/2001
(Continued)

OTHER PUBLICATIONS

Doi, K. "Current Status and Future Potential of Computer-Aided Diagnosis in Medical Imaging" The British Journal of Radiology, vol. 78, 2005, pp. S3-S19.

(Continued)

*Primary Examiner* — Jack Berman
*Assistant Examiner* — David E Smith

(57) ABSTRACT

A computer-aided method (30) comprises alternating between one or more of (i) navigational tasks and (ii) measuring, qualification, and quantification tasks of a clinical task in accordance with defined simple click style user interactions. The defined simple click style user interactions are based upon a domain knowledge (34) that includes (i) details of an anatomy and (ii) details of a clinical measurement, quantification, or workflow of the clinical task associated with the anatomy. Responsive to execution of a simple click style user interaction within a current view (36), and further in accordance with a corresponding navigational task or measuring, qualification, or quantification task, the method transitions within the clinical task and its workflow between one or more of (a) a first measurement point and a next measurement point within the current view (36) or (b) the current view (36) and a next view (38).

21 Claims, 6 Drawing Sheets

(51) Int. Cl.
*A61B 5/055* (2006.01)
*A61B 6/03* (2006.01)

(56) References Cited

U.S. PATENT DOCUMENTS

| | | | |
|---|---|---|---|
| 2002/0024530 A1* | 2/2002 | Van Liere | 345/700 |
| 2002/0067340 A1 | 6/2002 | Van Liere | |
| 2002/0183607 A1 | 12/2002 | Bauch | |
| 2003/0016850 A1* | 1/2003 | Kaufman et al. | 382/128 |
| 2004/0047497 A1* | 3/2004 | Daw et al. | 382/128 |
| 2004/0171922 A1* | 9/2004 | Rouet et al. | 600/407 |
| 2005/0228250 A1* | 10/2005 | Bitter et al. | 600/407 |
| 2006/0204067 A1* | 9/2006 | Tuma et al. | 382/128 |

FOREIGN PATENT DOCUMENTS

| | | |
|---|---|---|
| EP | 1085332 A2 | 3/2001 |
| JP | 2001137237 A | 5/2001 |
| JP | 2005520590 A | 7/2005 |

OTHER PUBLICATIONS

Testi, Debora et al "JIDE: A New Software for Computer-Aided Design of Hip Prosthesis" Computer Methods and Programs in Biomedicine 2004, Vo. 75, pp. 213-220.

* cited by examiner

METHOD AND APPARATUS FEATURING SIMPLE CLICK STYLE INTERACTIONS ACCORDING TO A CLINICAL TASK WORKFLOW

The present embodiments relate generally to medical systems and more particularly, to a method and apparatus featuring click-and-go clinical task workflow interactions.

To cope with the growing number of slices that current modalities like computer tomography (CT) and magnetic resonance (MR) provide, Picture Archive and Communications System (PACS) terminals and image processing workstations are equipped with volume rendering or visualization capabilities. These volume rendering and visualization techniques combine the information contained in the slices so that the user can deal with the emerging information overload and also get feedback on how the currently observed data is oriented in the patient's anatomy. A PACS terminal or workstation is used to store and retrieve medical images. The functionalities of PACS systems and medical image processing workstations have only recently begun to evolve together.

Volume visualization tools that offer direct volume rendering, surface volume rendering, gradient volume rendering, in addition to maximum intensity projection (MIP), minimum intensity projection (mIP) and average, need some way to interact with the view geometry in order to orientate the projection plane (i.e., the window the user is looking at). Interactions may include functions like zoom, pan, roll, and rotate. These functions can be provided through user interface elements like sliders or edit boxes or in a more 'direct' way using direct mouse manipulation (DMM). In DMM, the geometric functions are selected through combinations of mouse buttons or by a click-able icon in the image. For example, dragging the mouse pointer can alter the value of the selected parameter. In addition, horizontal and vertical movements can be mapped to different features. Accordingly, volume visualization provides a fast way to inspect or quickly scan through visualization data. In combination with the original slices, the volume visualization assists the radiologist and other specialists to diagnose their patients within reasonable time. Volume visualization thus provides a way to assist in an appropriate diagnosis.

Besides viewing, clinical users use the visualization tools to also perform measurements in the data, referred to herein as quantification. In particular, the volume rendering techniques in combination with the geometry manipulation schemes (such as DMM) are used to navigate through the visualization data. Once an acceptable view is found, anatomical landmarks (or supporting graphics) are positioned and edited using a pointer. For example, measuring applications often involve positioning and editing of anatomical landmarks or other supporting graphics like points (for example: the center of a joint or bone), lines (for example: tangents to, or edges from, or axes of anatomical structures), contours (for example: delineating certain anatomical parts), planes (for example: though the axis and neck of the femoral bone) or balls (for example: modeling of joints). However, navigating and placing points of interest using DMM based navigation is not an easy process. It takes a lot of user interactions, requires a powerful PC and it often delivers very ambiguous results.

Three-dimensional (3D) anatomical landmarks or other types of supporting graphics can be entered in two-dimensional (2D) slices (the exact 3D position can then easily be calculated) or on slabs or complete volumes as long as the rendering mode has a depth for each pixel in the projection plane, for example, a surface volume rendering or a MIP. For images that have no clearly defined depth, like average intensity projection or a direct volume rendering, it is not possible to place a landmark on that image directly.

Besides entering anatomical landmarks and supporting graphics, it should also be possible to edit them. However, editing of these landmarks in 3D is a very difficult task. Depending on the orientation of a projection plane, the interaction behavior could be different for different orientations of the projection plane. That is, there may exist a number of possible techniques for drawing and editing in 2D and 3D images.

Furthermore, as discussed above, current visualization solutions utilize volume rendering techniques in combination with the geometry manipulation schemes (such as DMM) to navigate through the visualization data. Once an acceptable view is found, anatomical landmarks or supporting graphics are positioned and edited within the view using a pointer (for example, a mouse pointer). It noted that the landmark is positioned on the depth that corresponds to the current rendering. To make editing easier, it is possible to show the landmarks in an orthoviewer. An orthoviewer is a tool in which the 3D volume is presented as three orthogonal slices. In such a case, the user is provided with additional feedback of the landmarks 3D position.

Moreover, the 3D landmarks are visible in all views. To provide some clue regarding the actual position of the landmarks, the landmark representations are drawn differently depending on the respective landmark's position relative to the current projection plane. For slice or slab renderings, using prior techniques, the landmarks in the projection plane are each drawn as a large cross; landmarks beyond the projection plane are each drawn as a smaller cross; and landmarks before the projection plane are each drawn as a large 'dotted' cross. For surface volume renderings, the landmarks can be visualized on top of the surface. Other techniques to add a depth impression to the visualized landmarks are depth shading and depth scaling of the landmark size or label.

The current approach of DMM navigation and anatomical landmark positioning has a number of problems. For example, it takes a lot of time with DMM to navigate to a correct view in order to start the placing of anatomical landmarks. While such a time consuming exploratory navigation may not be a problem when the user is creating an image for a presentation, but it can be a big problem in routine clinical practice. DMM also requires a powerful CPU in order to be interactive, thus making DMM less suitable for PACS systems or web based applications.

DMM offers generic tooling to navigate through the visualization data, while in clinical practice the user wants to navigate along certain features or previously defined landmarks. Furthermore, DMM ignores the type of quantification to be done. That is, DMM is more like a generic tool that is not solution driven. Moreover, DMM still uses a 'mode' such as roll, zoom, rotate, pan, opacity, slab thickness, etc., which corresponds to too many options and removes the 'Direct' from DMM.

Still further, when repeating a measurement, it is almost impossible to obtain the same view orientation ands thus get a consistent landmark position. When initiating an edit action of a landmark in a different view orientation than the one in which it was created, it is not clearly defined as to what should happen. In current slab based projection implementations, the landmark jumps to the depth defined for the current plane as soon as it is moved, thus making it almost impossible to edit these 3D landmarks.

When drawing a line on a MIP or mIP, it is impossible to predict the direction of the resulting line. Point based measurements on a MIP or mIP will have an unpredictable depth since the depth is not visible on the image. Furthermore, multiple orientations will be needed simultaneously to adequately position a 3D landmark.

Accordingly, an improved method and system for overcoming the problems in the art is desired.

According to an embodiment of the present disclosure, a computer-aided method comprises alternating between one or more of (i) navigational tasks and (ii) measuring, qualification, and quantification tasks of a clinical task in accordance with defined simple click style user interactions. The defined simple click style user interactions are based upon a domain knowledge that includes (i) details of an anatomy and (ii) details of a clinical measurement, quantification, or workflow of the clinical task associated with the anatomy. Responsive to execution of a simple click style user interaction within a current view, and further in accordance with a corresponding navigational task or measuring, qualification, or quantification task, the method transitions within the clinical task and its workflow between one or more of (a) a first measurement point and a next measurement point within the current view or (b) the current view and a next view. The method can also be implemented by a clinical workstation or system for implementing a clinical task, as well as in the form of a computer program product.

Figure 6:
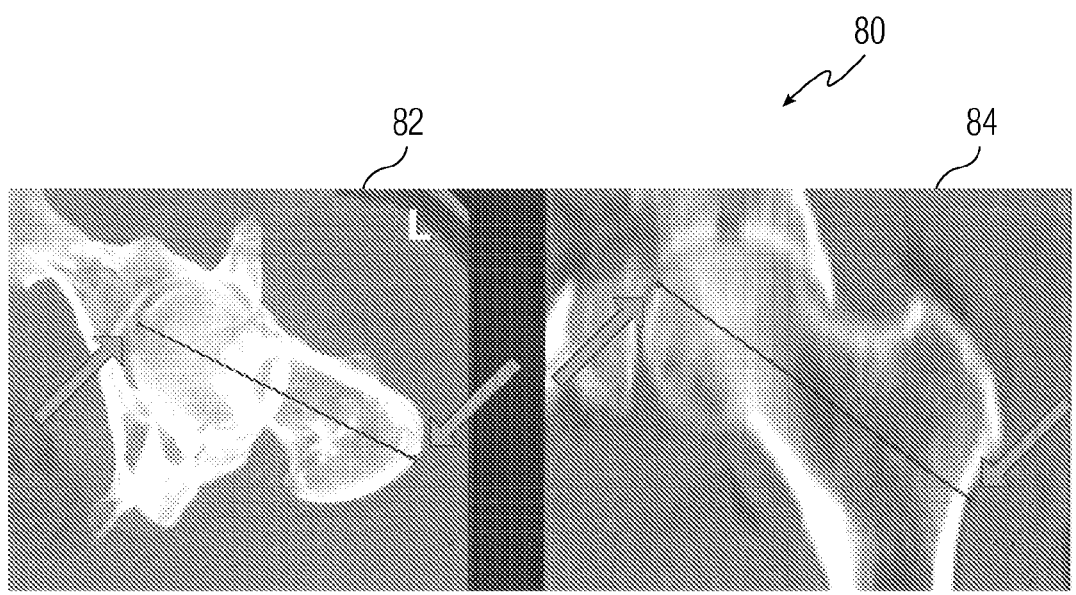
Figure 7:
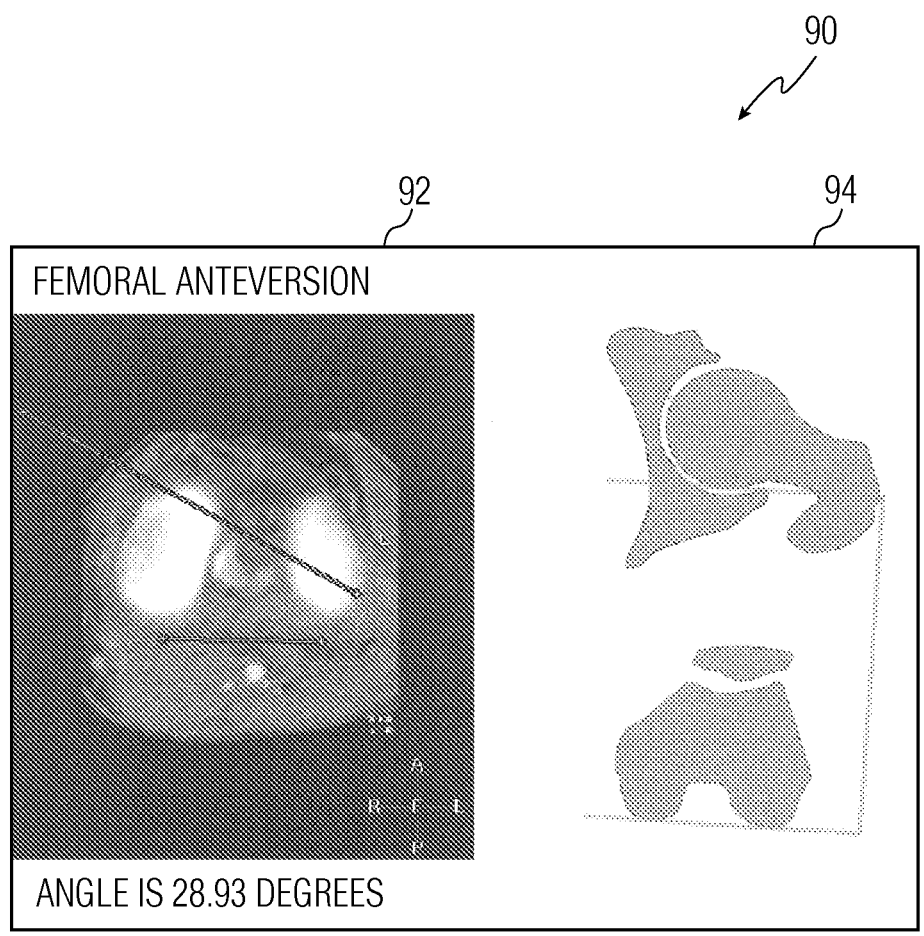
Figure 8:
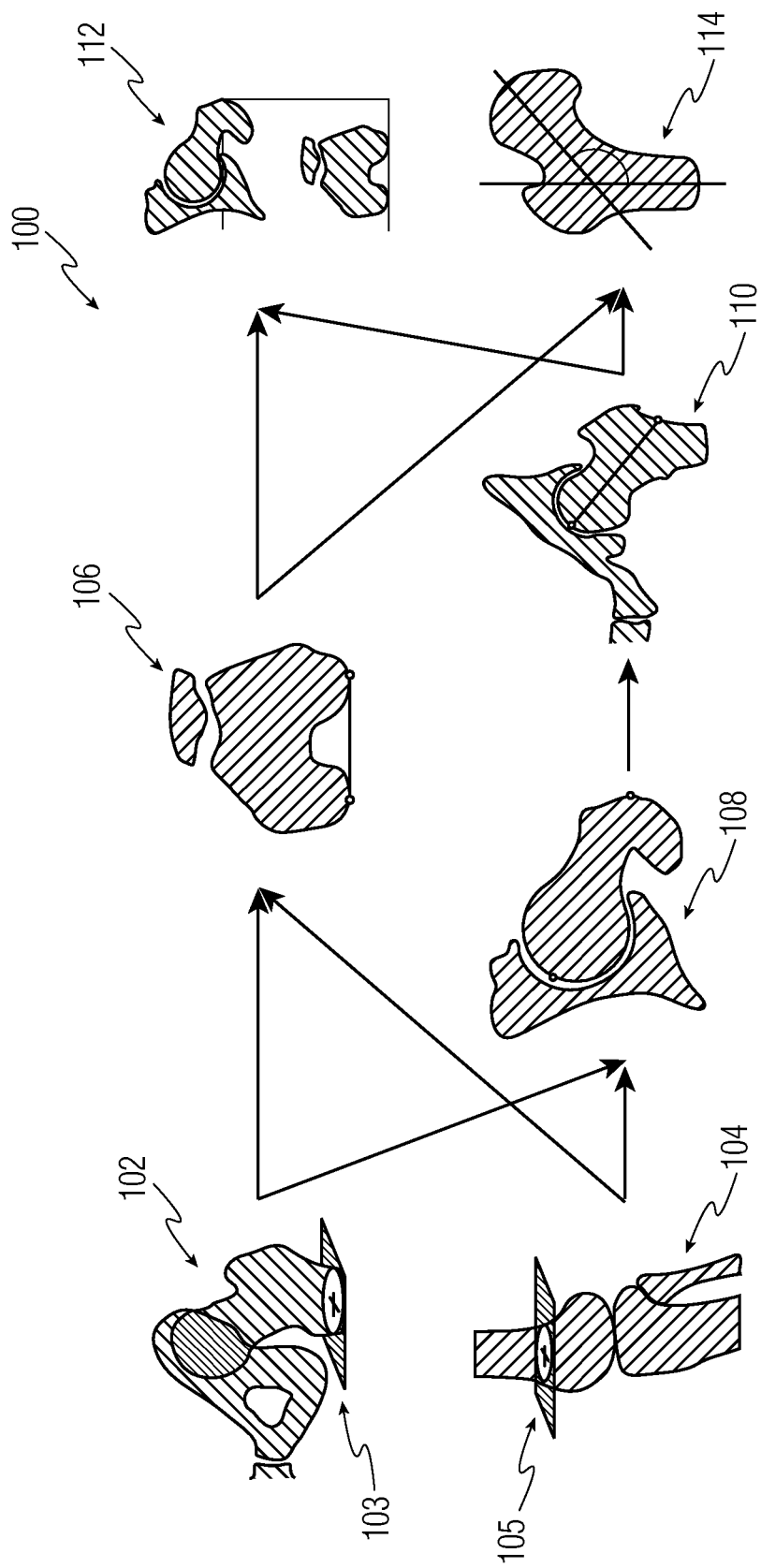

FIGS. 3-7 are illustrative views of steps in a workflow example for determining femoral rotation, showing a current view and for use in describing an interaction or interactions on the corresponding current view, further for indicating how the method proceeds to a next step in the workflow, using the method and apparatus featuring click-and-go clinical task workflow interactions according to one embodiment of the present disclosure; and FIG. 8 is a workflow overview illustrating the example presented in FIGS. 3-7 of the method and apparatus featuring click-and-go clinical task workflow interactions according to an embodiment of the present disclosure.

In the figures, like reference numerals refer to like elements. In addition, it is to be noted that the figures may not be drawn to scale.

According to one embodiment of the present disclosure, a method and apparatus featuring simple click style (or click-and-go) clinical task workflow interactions uses domain (or application) knowledge, including anatomy and details on the clinical measurement or quantification tasks and its workflow, to alternate between (i) navigational tasks and (ii) measuring, qualification and quantification tasks in an intelligent manner. The navigational tasks and measuring, qualification and quantification tasks can include, for example, region of interest (ROI) selection, supporting-graphics drawing and anatomical landmark placement. In this way, the need for the time-consuming DMM navigation and the ambiguity of the placement and edit actions can be advantageously avoided.

Figure 1:
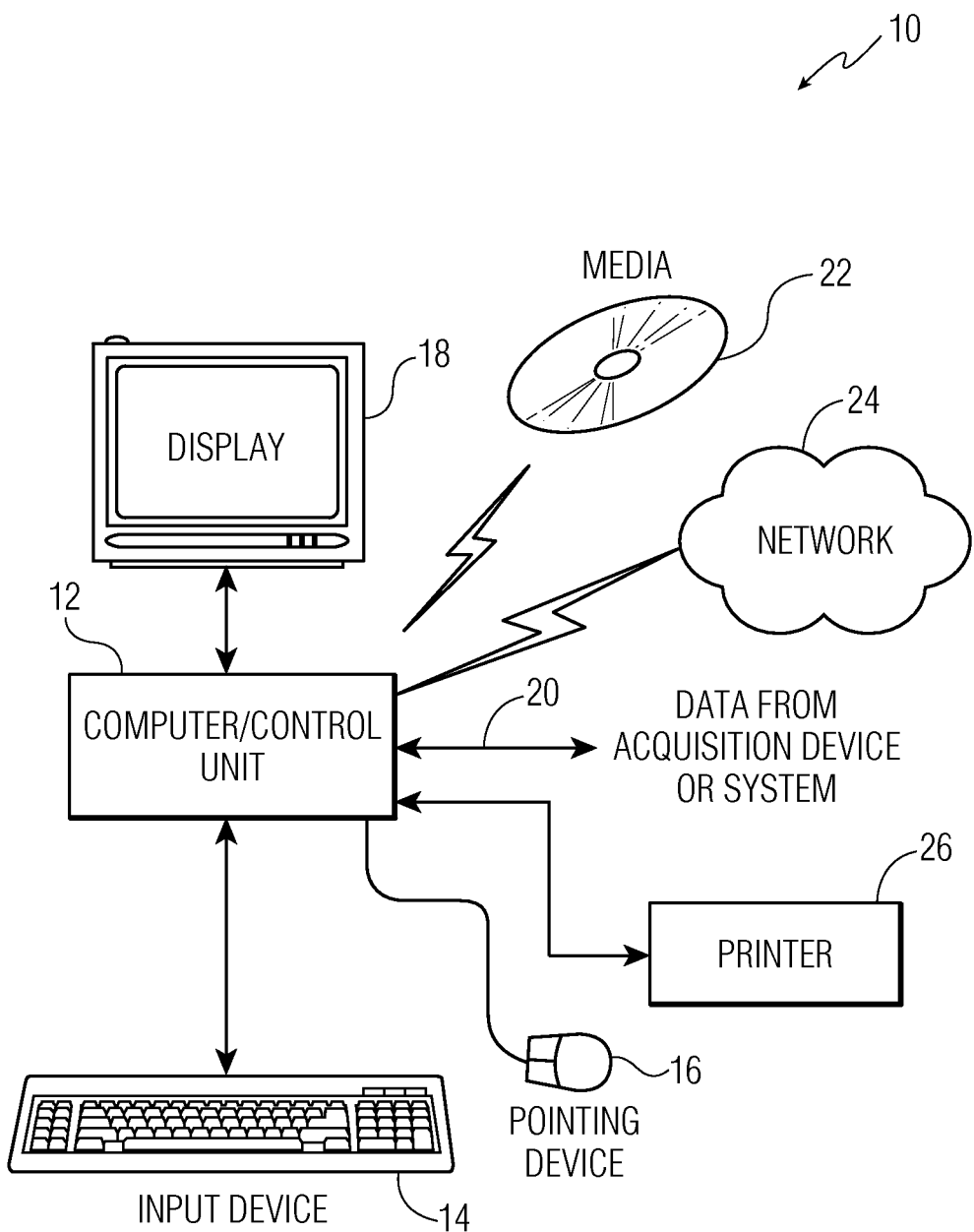
FIG. 1 is a partial block diagram view of a method and apparatus featuring click-and-go clinical task workflow interactions according to an embodiment of the present disclosure.

Turning now to the figures, FIG. 1 is a partial block diagram view of an apparatus 10 featuring simple click style clinical task workflow interactions according to an embodiment of the present disclosure. Apparatus 10 includes a computer/control unit 12, an input device 14, a pointing device 16, and a display 18. Computer/control unit 12 comprises any suitable computer and/or control unit that can be configured for performing the various functionalities as discussed herein with respect to the method featuring click-and-go clinical task workflow interactions. In addition, programming of the computer/control unit 12, for performing the methods according to the embodiments of the present disclosure as discussed herein, can be accomplished with use of suitable programming techniques. Furthermore, computer/control unit 12 interfaces with input device 14 (such as a keyboard, audio/voice input device, or similar device), pointing device 16 (such as a mouse, touch screen, or similar device) and display device 18, the computer/control unit for providing imaging data signals to the display for visual display.

The computer/control unit 12 may receive data from one or more acquisition device and/or system (not shown), in addition to sending data to one or more device and/or system (not shown), via signal line 20. Signal line 20 can comprise any suitable signal line or lines (wire, wireless, optical, etc.). The computer/control unit 12 may also send/receive data from one or more of a mass storage device or media 22, and/or a computer network 24 (i.e., for remote data acquisition, storage, analysis, and/or display), etc., via suitable signaling apparatus (not shown). Still further, system 10 may include a printer device 26 coupled to computer/control unit 12 for suitable use, as may be desired, during a particular clinical task or other procedure involving use of apparatus 10.

Figure 2:
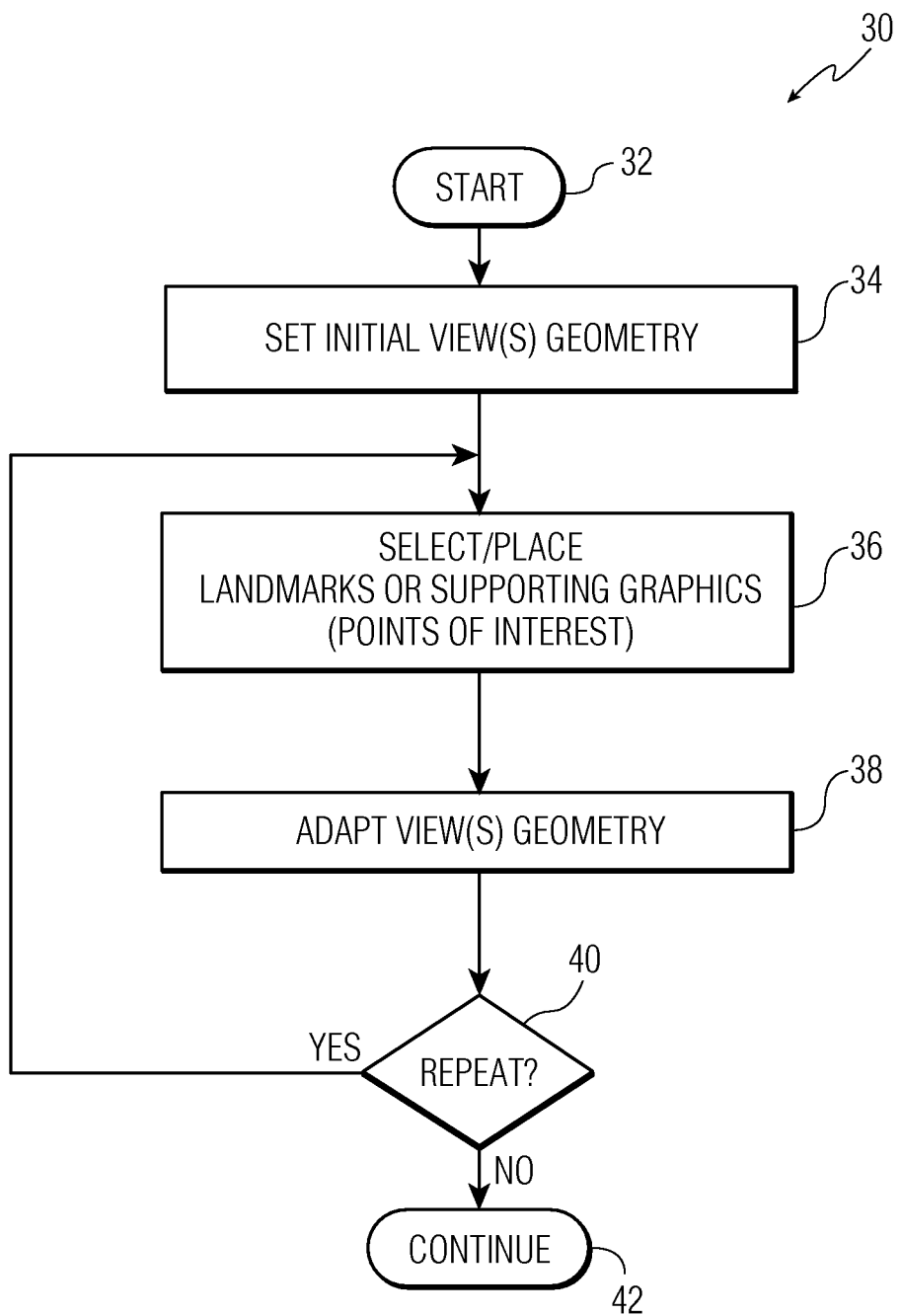
FIG. 2 is a flow diagram view illustrating a method featuring click-and-go clinical task workflow interactions according to an embodiment of the present disclosure.

FIG. 2 is a flow diagram view illustrating a method 30 featuring click-and-go clinical task workflow interactions according to an embodiment of the present disclosure. The process 30 of the click-and-go approach according to one embodiment of the present disclosure includes: set initial view(s) geometry 34; select/place landmarks or supporting graphics (points of interest) 36; adapt view(s) geometry 38; and then repeat 40 for as long as needed to complete a workflow of a current clinical task or clinical procedure. If in step 40, the workflow for the current clinical task is not finished, then the method repeats step 36 and step 38 until the workflow is finished. If in step 40, the workflow is finished, then the method advances to step 42. Step 42 can represent either an end to the current clinical task processing or a continuation of processing for additional purposes, as may be appropriate for a given clinical application.

According to one embodiment of the present disclosure, each clinical task will define an initial view (or views). Selection clicks or anatomical landmarks or supporting graphics (hereinafter, referred to as points of interest (POI)) that were defined in the respective view) will determine the new geometry (or geometries) of the new view (or views) in a subsequent step. In the new view (or views), new points of interest can again be defined (via a selection click), wherein the process is repeated as necessary according to the workflow of a given clinical task.

According to another embodiment of the present disclosure, the interaction possibilities of a view are reduced to a minimum with use of apparatus 10 for clinical tasks. If there are interactions possible, then the interactions are defined relative to the current context, i.e., of the corresponding view (e.g., projection plane). For example, a slider can be allowed to shift the position of a visualized slice along a previously defined axis. Accordingly, the tools using this approach avoid use of DMM interactions because the DMM interactions give no direct information on the current value or the possible range of the controlled parameter. According to an embodiment of the present disclosure, interactions with points of interest are made to be constrained to the view that such points of interest were created in. If the current view is a slab, then a point corresponds to a perpendicular line to the current projection plane orientation, and a line corresponds to a perpendicular plane. In this way, interactions with the points of interest will be unambiguous.

As discussed herein, the embodiments of the present disclosure provide a number of advantages. For example, one advantage is that the system user does not have to use DMM to position a view for placing the points of interest. Instead, the method according to the embodiments of the present disclosure uses the context of the clinical task to define the initial view (or views) and the mapping of the points of interest to the subsequent view orientation (or orientations). Accordingly, the method provides a form of click and continue (referred to herein as "click-and-go") user interface. Stated another way, the method comprises click-and-go clinical task workflow interaction user interface for transitioning from a current view to the next view according to the requirements of the particular clinical task and its workflow.

Another advantage of the method according to the embodiments of the present disclosure is that editing of points of interest is possible unambiguously because every point of interest has a fixed orientation context with respect to a given projection plane view. Furthermore, the measurement or quantification results are more reproducible. If there is navigation, it will be along a clinically relevant orientation. That is, the method and apparatus make use of a workflow navigation that is determined according to (or along) a clinically relevant orientation. In other words, the degree of freedom is made clear from the view (i.e., the projection plane view), given that no ambiguity is allowed.

Further advantages of a one click workflow according to the embodiments of the present disclosure include that the method is task oriented, rendering the method is suitable for being implemented with a PACS/web interface. The method also can be easily customized to adjust to customer/task requirements.

FIGS. 3-7 provide a workflow example of an orthopedic measurement for determining the internal rotation of the femoral bone. With this measurement, an orthopedic surgeon quantifies the angle between the femoral neck and the femoral condyles axis. In this discussion, several examples of the alternations between the points of interest and the geometry of the views are encountered. Note that while FIGS. 3-7 are illustrative views of only one clinical task workflow example, other examples are possible for using the method and apparatus featuring click-and-go clinical task workflow interactions.

Figure 3:
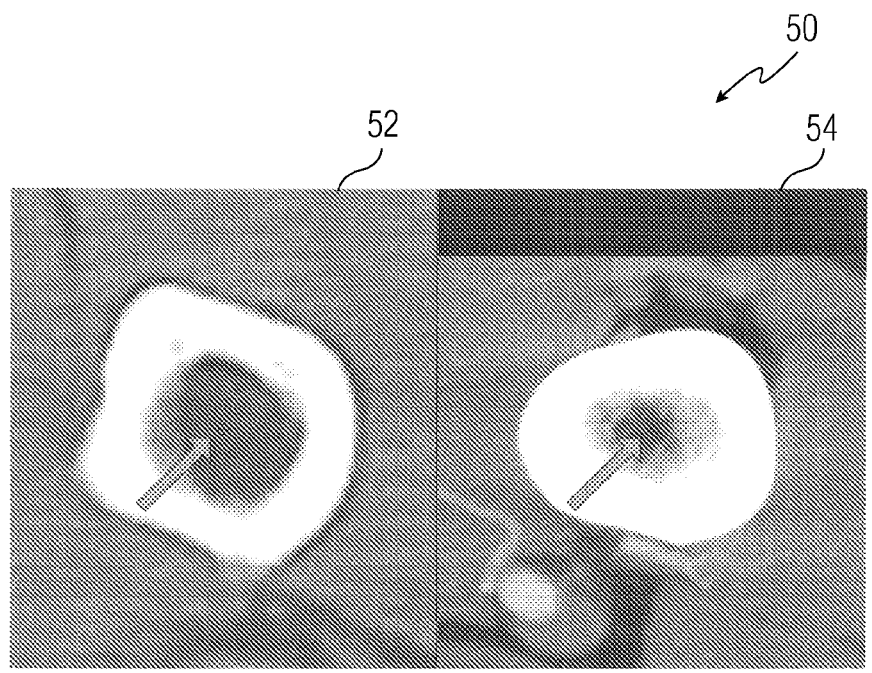
Figure 4:
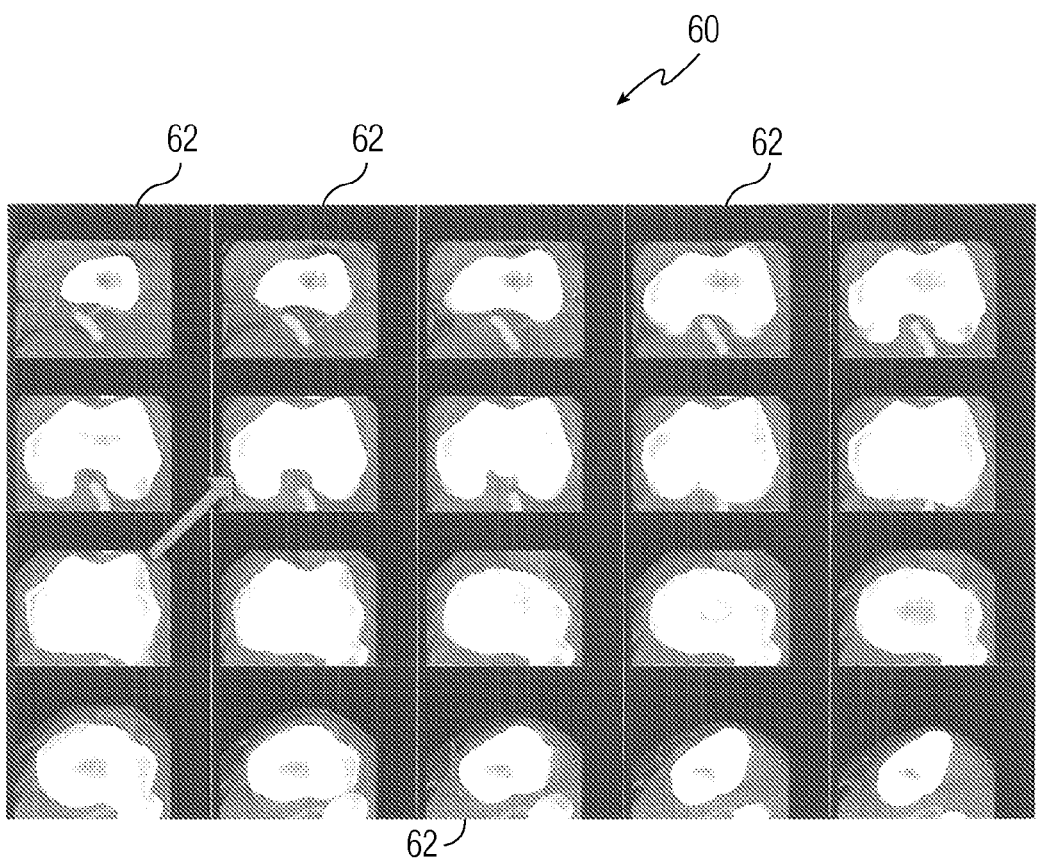

For the orthopedic application of the example illustrated in FIGS. 3-7, it involves two sub-volumes, one around the knee and one around the hip. Optionally there is one volume containing the entire femoral bone, however, it will not be considered for this example. In a first step, the system user identifies which volume contains the knee and which volume contains the hip, if the respective information is not already enclosed in the image information. The initial view 50 comprises two transversal slices 52 and 54, which are aligned with the original image stack, showing the proximal and the distal parts of the femur. In both slices, the user marks the center of the femoral bone (as shown in FIG. 3). After entering the points, the view updates its center and zoom settings allowing the user to refine the selection. These two points of interest form the femoral (anatomical) axis. In the following step, two composite views (only one of which is shown in FIG. 4) are generated that show an array 60 of thumbnail images 62 containing thick slabs along the femoral axis directory (each on a slightly different height). The user can select the correct slabs at knee and hip level by clicking the corresponding thumbnail. It is noted that the knee composite is shown in FIG. 4.

In other words, for view 50 of FIG. 3, the method includes establishing initial views 52 and 54 containing transversal slices of the femur. A system user then selects the proximal center (as illustrated by the arrow in the left image 52) and distal center (as indicated by the arrow in the right image 54) of the femoral axis, via respective simple click style selections. Responsive to selection of the proximal center and the distal center, the method continues by providing a thumbnail slab depth selector 60 aligned with the femur axis, for example, as shown in FIG. 4. A system user then selects, via a simple click style selection, one of the slabs 62, for example, in FIG. 4 corresponding to a correct slab at knee level showing both condyles (as indicated by the arrow showing the selected one).

Figure 5:
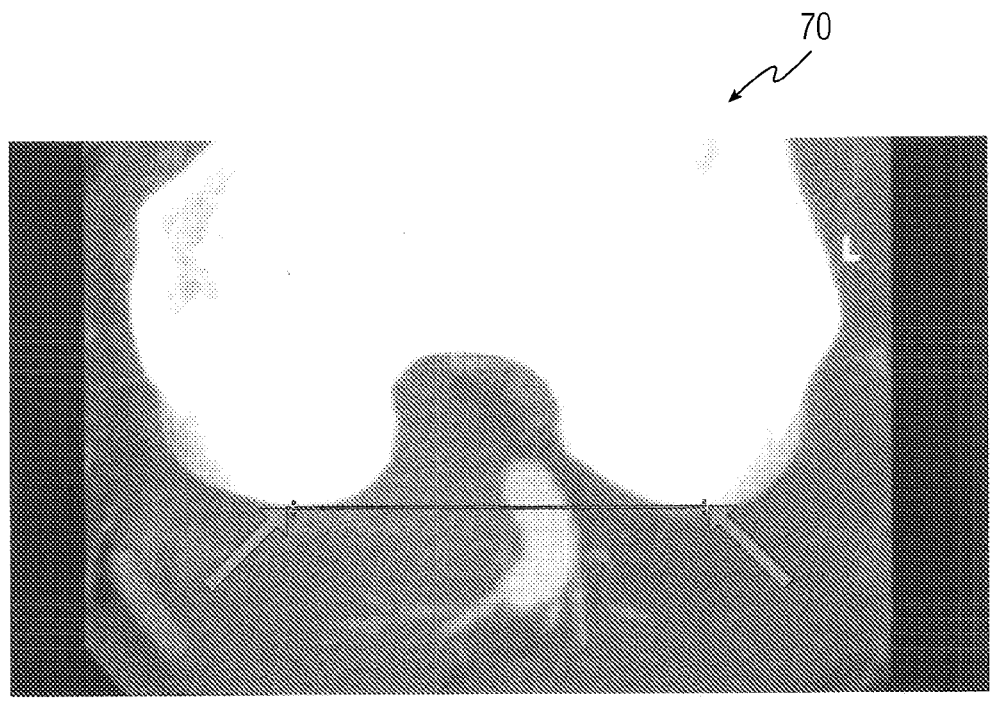

FIG. 5 is a view 70 illustrating a perpendicular slab selected from the thumbnail selector portion of FIG. 4 at the knee level. On the knee level slab, the system user is required to draw a line touching the posterior aspects of both femoral condyles. This corresponds to drawing the condylar tangent plane, wherein the tangent points are indicated by arrows proximate opposite ends of the line. In other words, the line corresponds to a tangent line which is actually a plane perpendicular to the femur anatomical axis.

FIG. 6 is a view 80 illustrating another perpendicular slab selected at a second depth level in another portion of the method featuring click-and-go clinical task workflow interactions according to an embodiment of the present disclosure. In particular, FIG. 6 illustrates a set up of the selected slab at the hip level, wherein the hip level slab was selected by way of a thumbnail selection (not shown) similar to that as illustrated and described with respect to FIG. 4. Further with the example, the user draws a line, via simple click style selections of a start point and an end point, through the femoral neck, as shown in FIG. 6. That is, on the selected hip slab, the system user is required to draw a line through the femoral neck. The line through the femoral neck is actually a plane though the neck. The left image 82 of FIG. 6 comprises a slab aligned with the femoral axis as selected in the thumbnail depth selector showing the femoral neckline plane. The arrows within image 82 show the selected line start and end points of the femoral neckline plane. The right image 84 of FIG. 6 comprises a slice based on the plane defined in the left image 82 showing the femoral neckline, wherein the arrows in image 84 show the selected line start and end points. In a following step (FIG. 7), the view in FIG. 5 is aligned with the neck plane (i.e., corresponding to a thin slice) of FIG. 6.

FIG. 7 is a view 90 illustrating another image of yet another portion of the method featuring click-and-go clinical task workflow interactions according to an embodiment of the present disclosure. In particular, FIG. 7 illustrates a set up of an image perpendicular to the femoral axis. The internal rotation of the femoral bone is defined as the angle between the two lines in this perpendicular plane. The left image 92 comprises an image perpendicular to the femoral axis showing a slice at knee level with the projected axes and the measurement for the internal rotation of the femur (also called femoral anteversion). The right image 94 comprises a drawing explaining the measurement. Alternatively, the view 90 could have includes a set up of an image perpendicular to the femoral axis corresponding to merging the slab containing the condylar tangent and the slab containing the femoral neckline. That is, in this alternate view, both the condyle tangent and the femoral neckline are projected on a plane perpendicular to the femoral axis.

FIG. 8 is a workflow overview 100 illustrating the example of FIGS. 3-7 assembled together in one view. FIG. 8 contains the workflow of a clinical application for determining the internal rotation of the femur and the CCD angle. The CCD angle is the angle between the femoral axis and the femoral neck line. As shown, the steps include at 102, the selection of a slice and center point landmark 103 at a first depth, for example as discussed herein above with respect to FIG. 3. At 104, the steps include the selection of a slice and center point landmark 105 at a second depth, for example as discussed herein above with respect to FIG. 3. With the axis following from the landmarks of 103 and 105, the slabs of 106 (FIGS. 4 and 5) and of 108 (FIG. 6) are defined. With this same axis and the line from slab 108, plane 110 is defined and the femoral neck line is indicated. Combining the lines (i.e., conylar tangent and neck line) gives the internal femoral rotation of 112 (FIG. 7) and alternatively the CCD angle measurement from 114. Accordingly, the method featuring click-and-go clinical workflow interactions of FIG. 8 provide a clinical application viewer with a one click workflow that uses steps that are simple and small, and that require only minimal interaction.

Accordingly, the steps of the point and click computer-aided method as discussed herein are simple in that they are restricted to a handful of simple clicks, thereby restricting the user interface (UI) to a bare minimum. Accordingly, the steps render the need for a full fledged volume viewer and DMM unnecessary.

In one embodiment, a computer-aided method comprises alternating between one or more of (i) navigational tasks and (ii) measuring, qualification, and quantification tasks of a clinical task in accordance with defined simple click style user interactions, wherein the defined simple click style user interactions are based upon a domain knowledge that includes (i) details of an anatomy and (ii) details of a clinical measurement, quantification, or workflow of the clinical task associated with the anatomy; and responsive to execution of a simple click style user interaction within a current view, and further in accordance with a corresponding navigational task or measuring, qualification, or quantification task, the method transitions within the clinical task and its workflow between one or more of (a) a first measurement point and a next measurement point within the current view or (b) the current view and a next view.

In another embodiment, each simple click style user interaction comprises an unambiguously defined interaction that is restricted to a given view. The current view can comprise one or more of a projection image, a slab maximum intensity projection (MIP), a surface rendering, or a volume rendering. The current view may also contain an image rendering of an object upon which a respective simple click style user interaction associated with the current view is defined unambiguously. In addition, the workflow may comprise measuring steps that can be interchanged with view positioning steps, further wherein the measuring steps and view positioning steps each comprise one or more unambiguously defined simple click style user interactions.

According to another embodiment, the method further includes, responsive to the simple click style user interaction, processing of information content within the current view unambiguously for determining a content of the next view. In addition, an initial current view can comprise a default view.

According to yet another embodiment, the method comprises rendering a first view geometry on a projection plane, wherein the first view geometry comprises one of an initial view geometry or initial view geometries determined as a function of (i) the domain knowledge and (ii) data representative of a number of slices of a volume, the data being a function of a particular volume rendering modality. The method further includes alternating between (i) navigational tasks or (ii) measuring, qualification and quantification tasks for the prescribed clinical measurement in connection with (a) the first view geometry or (b) a subsequent view geometry, wherein alternating is in response to a simple click style user interaction with the projection plane; rendering a subsequent view geometry on a subsequent projection plane further in response to another simple click style user interaction with the projection plane; and repeating the alternating and rendering of the subsequent view geometry on the subsequent projection plane for a duration of processing according to the requirements of a given clinical task.

As used herein, the terms display, screen, projection plane, and view describe the visualized 2D representation of the actual 3D object (e.g., the anatomy). The process of transforming the 3D object to the 2D representation is called projecting (i.e., which comprises only the coordinate transformation itself) or rendering (i.e., which also includes colors, lighting, etc.). The transformation itself is often described as the rendering/projection mode or view geometry. Examples of a view geometry can include: perspective projection, orthogonal projection or more complex renderings like curved planar reformats. Interactions are on the projection plane (or screen). A mouse click is translated back (i.e., the inverse of the rendering) to an actual 3D position in the anatomy using the 2D position on the screen and the projection mode (i.e., view geometry). For example, in some instances, like in the example with the knee slab, the process does not always go back to 3D anatomy coordinates: the tangent line drawn on a slab is used as a plane perpendicular to the slab. In this instance, clicks cannot be mapped back to actual 3D coordinates because a slab has no clearly defined depth.

In the embodiment of the previous paragraph, the subsequent view geometry can comprise one of an adapted view geometry or adapted view geometries determined as a function of (i) the domain knowledge of the prescribed clinical measurement, (ii) the visualization data, and (iii) one of (a) navigational tasks or (b) measuring, qualification and quantification tasks of the prescribed clinical measurement selected in response to the click-and-go interaction with the projection plane.

In a further embodiment, the current view corresponds to a currently available view displayed on a display screen. In addition, the (i) navigational tasks and (ii) measuring, qualification and quantification tasks can include one or more of selecting anatomical landmarks, placing anatomical landmarks, selecting supporting graphics, and placing supporting graphics on the current view. Furthermore, the method can further comprise implementing the method via an Internet web interface.

Moreover, in one embodiment, the clinical task can comprise an orthopedic measurement for determining an internal rotation of a femoral bone and for quantifying an angle between a femoral neck axis and a femoral condyles axis. The first view geometry can comprise first and second images of two stack-aligned slices, wherein the first stack-aligned slice is representative of a first elevation level and the second stack-aligned slice is representative of a second elevation level. In addition, a first simple click style user interaction can comprise a selection of first and second center points in respective ones of the first and second stack-aligned slices, and wherein a subsequent view geometry comprises first or second thumbnail selector views, wherein each of the first and second thumbnail selector views comprises a series of thumbnail images of slabs that are perpendicular to a femoral axis defined by the first and second center points. Still further, the selecting of a desired slab of the first or second thumbnail selector views can comprise moving a pointer or position highlighter to be positioned over the desired slab and clicking on the pointer or position highlighter while the pointer or position highlighter is positioned over or highlighting the corresponding thumbnail selector view.

According to a further embodiment, the method is as discussed herein, wherein the simple click style user interaction comprises an interaction with a projection plane and defined as a function of the workflow relative to a current context of the projection plane. The method is further as discussed herein, wherein the simple click style user interaction comprises an interaction with a projection plane and with one or more points of interest within the projection plane, wherein the one or more points of interest have a fixed orientation context, the fixed orientation context being constrained to a given projection plane view in which such one or more points of interest were created. The method is still further as discussed herein, wherein a current view comprises an image of a slab, and wherein a landmark in the form of a point on the current view represents a line perpendicular to the slab of the current view, and wherein a landmark in the form of a line on the current view represents a plane perpendicular to the slab of the current view.

According to another embodiment, a clinical task apparatus comprises a display; a computer/control unit coupled to the display, wherein the computer/control unit provides data to the display for rendering a projection view; and an input device coupled to the computer/control unit for providing user inputs to the computer/control unit, wherein the computer control unit is programmed with instructions for carrying out the method featuring simple click style clinical task workflow interactions as discussed herein.

According to yet another embodiment, a computer program product comprises computer readable media having a set of instructions that are executable by a computer for carrying out the method featuring click-and-go clinical task workflow interactions as discussed herein.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be applied to simple click style (click-and-go) interaction used in the areas of volume visualization, navigation, and three-dimensional (3D) measurement and quantification applications in PACS systems and/or clinical workstations. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A computer-aided method comprising:
alternating between one or more of (i) navigational tasks and (ii) measuring, qualification, and quantification tasks of a clinical task in accordance with defined user click interactions, wherein the defined user click interactions are based upon a user domain knowledge that includes (i) details of an anatomy and (ii) details of a workflow of the clinical task associated with the anatomy, wherein the workflow includes a plurality of steps; and
responsive to execution of a one-dimensional user click interaction within a current view and without any further user interaction, and further in accordance with a corresponding navigational task or measuring, qualification, or quantification task, transitioning within the clinical task and each new step in its workflow between one or more of (a) a first measurement point and a next measurement point within the current view or (b) the current view and a next view, wherein the user click interaction comprises only a single click wherein the view geometry is updated automatically each time a workflow task is performed.

2. The method of claim 1, wherein each user click interaction comprises an unambiguously defined interaction that is restricted to a given view.

3. The method of claim 1, wherein the current view comprises one or more of a projection image, a slab maximum intensity projection (MIP), a surface rendering, or a volume rendering.

4. The method of claim 1, wherein the current view contains an image rendering of an object upon which a respective user click interaction associated with the current view is defined unambiguously.

5. The method of claim 1, wherein the steps of the workflow comprises measuring steps that can be interchanged with view positioning steps, further wherein the measuring steps and view positioning steps each comprise one or more unambiguously defined user click interactions.

6. The method of claim 1, further wherein responsive to the user click interaction, information content within the current view is processed unambiguously for determining a content of the next view.

7. The method of claim 1, wherein an initial current view comprises a default view.

8. The method of claim 1, wherein the current view corresponds to a currently available view displayed on a display screen.

9. The method of claim 1, wherein the (i) navigational tasks and (ii) measuring, qualification and quantification tasks include one or more of selecting anatomical landmarks, placing anatomical landmarks, selecting supporting graphics, and placing supporting graphics on the current view.

10. The method of claim 1, further comprising: implementing the method via an Internet web interface.

11. The method of claim 1, wherein the user click interaction comprises an interaction with a projection plane and defined as a function of the workflow relative to a current context of the projection plane.

12. The method of claim 1, wherein the user click interaction comprises an interaction with a projection plane and with one or more points of interest within the projection plane, wherein the one or more points of interest have a fixed orientation context, the fixed orientation context being constrained to a given projection plane in which such one or more points of interest were created.

13. The method of claim 1, wherein a current view comprises an image of a slab, and wherein a landmark in the form of a point on the current view represents a line perpendicular to the slab of the current view, and wherein a landmark in the form of a line on the current view represents a plane perpendicular to the slab of the current view.

14. A computer aided method comprising:
alternating between one or more of (i) navigational tasks and (ii) measuring, qualification, and quantification tasks of a clinical task in accordance with defined user click interactions, wherein the defined user click interactions are based upon a user domain knowledge that includes (i) details of an anatomy and (ii) details of a clinical measurement, quantification, or workflow of the clinical task associated with the anatomy; and
responsive to execution of a one-dimensional user click interaction within a current view and without any further user interaction, and further in accordance with a corresponding navigational task or measuring, qualification, or quantification task, transitioning within the clinical task and its workflow between one or more of (a) a first measurement point and a next measurement point within the current view or (b) the current view and a next view, wherein the user click interaction comprises only a single click;
rendering a first view geometry on a projection plane, wherein the first view geometry comprises one of an initial view geometry or initial view geometries determined as a function of (i) domain knowledge and (ii) volume data provided by an image modality;
alternating between (i) navigational tasks or (ii) measuring, qualification and quantification tasks for the prescribed clinical measurement in connection with (a) the first view geometry or (b) a subsequent view geometry, wherein alternating is in response to a user click interaction with the projection plane;
rendering a subsequent view geometry on a subsequent projection plane further in response to another user click interaction with the projection plane; and
repeating the alternating and rendering of the subsequent view geometry on the subsequent projection plane for a duration of processing according to the requirements of a given clinical task.

15. The method of claim 14, wherein the subsequent view geometry comprises one of an adapted view geometry or adapted view geometries determined as a function of (i) the domain knowledge of the prescribed clinical measurement, (ii) the visualization data, and (iii) one of (a) navigational tasks or (b) measuring, qualification and quantification tasks of the prescribed clinical measurement selected in response to the click-and-go interaction with the projection plane.

16. The method of claim 14, wherein the clinical task comprises an orthopedic measurement for determining an internal rotation of a femoral bone and for quantifying an angle between a femoral neck axis and a femoral condyles axis.

17. The method of claim 16, wherein the first view geometry comprises first and second images of two stack-aligned slices, wherein the first stack-aligned slab is representative of a first elevation level and the second stack-aligned slab is representative of a second elevation level.

18. The method of claim 17, further wherein a first user click interaction comprises a selection of first and second center points in respective ones of the first and second stack-aligned slices, and wherein a subsequent view geometry comprises first or second thumbnail selector views, wherein each of the first and second thumbnail selector views comprises a series of thumbnail images of slabs that are perpendicular to a femoral axis defined by the first and second center points.

19. The method of claim 18, further wherein selecting a desired slab of the first or second thumbnail selector views comprises moving a pointer or position highlighter to be positioned over the desired slab and clicking on the pointer or position highlighter while the pointer or position highlighter is positioned over or highlighting the corresponding thumbnail selector view.

20. A clinical task apparatus comprising:
a display;
a computer/control unit coupled to the display, wherein the computer/control unit provides data to the display for rendering a projection view; and
an input device coupled to the computer/control unit for providing user inputs to the computer/control unit,
wherein the computer control unit is programmed with instructions for carrying out a method, comprising,
alternating between one or more of (i) navigational tasks and (ii) measuring, qualification, and quantification tasks of a clinical task in accordance with defined user click interactions received from the input device, wherein the defined user click interactions are based upon a user domain knowledge that includes (i) details of an anatomy and (ii) details of a workflow of the clinical task associated with the anatomy, wherein the workflow includes a plurality of steps; and
responsive to execution of a one-dimensional user click interaction with the input device within a current view, and further in accordance with a corresponding navigational task or measuring, qualification, or quantification task, automatically transitioning within the clinical task and each new step in its workflow between one or more of (a) a first measurement point and a next measurement point within the current view or (b) the current view and a next view, wherein the user click interaction comprises only a single click wherein the view geometry is updated automatically each time a workflow task is performed.

21. A computer program product comprising:
computer readable media having a set of instructions that are executable by a computer for carrying out a method, comprising,
alternating between one or more of (i) navigational tasks and (ii) measuring, qualification, and quantification tasks of a clinical task in accordance with defined user click interactions, wherein the defined user click interactions are based upon a user domain knowledge that includes (i) details of an anatomy and (ii) details of a workflow of the clinical task associated with the anatomy, wherein the workflow includes a plurality of steps; and
responsive solely to execution of a single one-dimensional user click interaction within a current view, and further in accordance with a corresponding navigational task or measuring, qualification, or quantification task, automatically transitioning within the clinical task and each new step in its workflow between one or more of (a) a first measurement point and a next measurement point within the current view or (b) the current view and a next view, wherein the user click interaction comprises only a single click wherein the view geometry is updated automatically each time a workflow task is performed.

* * * * *